United States Patent
Zhang et al.

(10) Patent No.: US 7,945,083 B2
(45) Date of Patent: May 17, 2011

(54) METHOD FOR SUPPORTING DIAGNOSTIC WORKFLOW FROM A MEDICAL IMAGING APPARATUS

(75) Inventors: Daoxian H. Zhang, Los Gatos, CA (US); Patrick B. Heffernan, Campbell, CA (US); Marco Bucci, Genoa (IT); Zhimin Huo, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 1026 days.

(21) Appl. No.: 11/440,929

(22) Filed: May 25, 2006

(65) Prior Publication Data

US 2007/0274585 A1    Nov. 29, 2007

(51) Int. Cl.
*G06K 9/00* (2006.01)
*A61B 5/05* (2006.01)
(52) U.S. Cl. ........................................ 382/132; 600/407
(58) Field of Classification Search .................... 382/132
See application file for complete search history.

(56) References Cited

U.S. PATENT DOCUMENTS

| | | | |
|---|---|---|---|
| 5,729,620 A | 3/1998 | Wang | |
| 5,805,118 A | 9/1998 | Mishra et al. | |
| 5,984,870 A * | 11/1999 | Giger et al. | 600/443 |
| 5,986,662 A * | 11/1999 | Argiro et al. | 345/424 |
| 5,987,345 A | 11/1999 | Engelmann et al. | |
| 6,058,322 A * | 5/2000 | Nishikawa et al. | 600/408 |
| 6,243,095 B1 * | 6/2001 | Shile et al. | 715/854 |
| 6,650,766 B1 | 11/2003 | Rogers et al. | |
| 6,734,880 B2 | 5/2004 | Chang et al. | |
| 6,801,645 B1 * | 10/2004 | Collins et al. | 382/130 |
| 6,819,785 B1 * | 11/2004 | Vining et al. | 382/128 |
| 6,925,200 B2 * | 8/2005 | Wood et al. | 382/132 |
| 6,970,587 B1 | 11/2005 | Rogers | |

(Continued)

FOREIGN PATENT DOCUMENTS

EP    1 398 721 A2    3/2004

(Continued)

OTHER PUBLICATIONS

M. N. Chong, "Concurrent Processing for Picture Archiving and Communication System (PACS)," Proceedings of IEEE Singapore International Conference on Singapore Jul. 3-7, 1995, pp. 468-472, XP010196131.

(Continued)

*Primary Examiner* — David P Rashid

(57) ABSTRACT

A method for supporting diagnostic workflow from a medical imaging apparatus. A set of at least two images are obtained from a patient and displayed according to a user-specified image display layout selected from a plurality of image display layouts. One or more markers are associated with a region of interest in the displayed images. A list of regions of interest is generated, each having an entry for each associated marker. A classification is assigned to each entry in the list of regions of interest according to health risk.

13 Claims, 14 Drawing Sheets

U.S. PATENT DOCUMENTS

| | | | |
|---|---|---|---|
| 2002/0101436 A1* | 8/2002 | Shastri et al. | 345/619 |
| 2003/0026503 A1 | 2/2003 | Kallergi et al. | |
| 2003/0174872 A1 | 9/2003 | Chalana et al. | |
| 2004/0052328 A1* | 3/2004 | Sabol et al. | 378/37 |
| 2004/0085443 A1* | 5/2004 | Kallioniemi et al. | 348/135 |
| 2004/0102689 A1 | 5/2004 | Metz et al. | |
| 2004/0122790 A1 | 6/2004 | Walker et al. | |
| 2004/0158409 A1* | 8/2004 | Teshima et al. | 702/22 |
| 2004/0247166 A1 | 12/2004 | Giger et al. | |
| 2005/0058350 A1* | 3/2005 | Dugan et al. | 382/224 |
| 2005/0207631 A1* | 9/2005 | Martens et al. | 382/131 |
| 2006/0004278 A1* | 1/2006 | Giger et al. | 600/408 |

FOREIGN PATENT DOCUMENTS

| | | |
|---|---|---|
| JP | 2004-113444 | 4/2004 |
| JP | 2005-169155 | 6/2005 |
| WO | WO 98/16903 | 4/1998 |
| WO | WO 99/05503 | 2/1999 |

OTHER PUBLICATIONS

Titled: "Dicom Adapter Service for CAD System", Filed May 25, 2006, Inventor: Heffernan et al.

Titled: Computer Aided Detection of Microcalcification Clusters, U.S. Appl. No. 11/284,570, inventor: Zhang et al., filed Nov. 22, 2005 and based on Provisional U.S. Appl. No. 60/631,154, filed Jan. 4, 2005.

Titled: "Automatic Image Contrast in Computer-Aided Diagnosis", U.S. Appl. No. 11/285,231, filed Nov. 22, 2005, based on Provisional U.S. Appl. No. 60/631,156, filed Nov. 24, 2004, Inventor Zhang et al.

* cited by examiner

METHOD FOR SUPPORTING DIAGNOSTIC WORKFLOW FROM A MEDICAL IMAGING APPARATUS

CROSS REFERENCE TO RELATED APPLICATIONS

Reference is made to commonly assigned application U.S. Ser. No. 11/440,978, entitled "DICOM ADAPTER SERVICE FOR CAD SYSTEM" by Heffernan et al., filed on common date herewith.

Reference is made to commonly assigned application U.S. Ser. No. 11/284,570, entitled "COMPUTER AIDED DETECTION OF MICROCALCIFICATION CLUSTERS" by Zhang et al., filed on Nov. 22, 2005, based on Provisional Patent Application No. 60/631,154, filed on Jan. 4, 2005.

Reference is made to commonly assigned application U.S. Ser. No. 11/285,231, entitled "AUTOMATIC IMAGE CONTRAST IN COMPUTER-AIDED DIAGNOSIS" by Zhang et al., filed on Nov. 22, 2005, based on Provisional Patent Application No. 60/631,156, filed on Nov. 24, 2004.

FIELD OF THE INVENTION

This invention generally relates to diagnostic medical imaging systems and more particularly relates to methods and apparatus for providing an improved workflow for display and use of diagnostic images, particularly for mammography.

BACKGROUND OF THE INVENTION

The benefits of computer-aided diagnosis (CAD) in radiology in general, and particularly in mammography, are widely recognized. To date, there has been considerable effort directed toward computer-aided methods that assist the diagnostician to correctly and efficiently identify problem areas detected in a mammography image and to improve the accuracy with which diagnoses are made using this information.

There have been a number of initiatives directed toward diagnostic image management, presentation, and delivery. One initiative is the DICOM (Digital Imaging and Communications in Medicine) standard, developed to effectively manage the potentially large amounts of patient data that are now available from a range of diagnostic and imaging systems. Developed and maintained as a joint effort through the National Electrical Manufacturers Association, the DICOM data interchange standard has the goal of providing a common framework for acquisition, transmission, archival, retrieval, and presentation of medical images and related patient data from a variety of imaging modalities and environments. Benefits from DICOM conformance are believed to include interoperability of equipment from different manufacturers so that patient data, once obtained, can be accessible for display, printing, diagnostic assessment, and storage, without requiring proprietary systems and software. For example, DICOM conformance allows mammography images from any of a number of different types of equipment to be processed on a single Computer-Aided Diagnosis (CAD) system. Results from the CAD system can then be stored and used for viewing or presentation by other conforming systems.

The DICOM standard defines data structures, communication protocols, and interaction models for data transfer between systems. While it is widely viewed that DICOM conformance offers considerable benefit to equipment manufacturers and systems providers as well as to medical professionals and the patients they serve, achieving conformance and compatibility between systems has proven to be a challenge. Even though efforts at conformance have been underway, seamless interoperability is not guaranteed because different vendors can implement different parts of the same large standard.

In an effort to facilitate DICOM inter-operability, an ongoing industry initiative entitled Integrating the Healthcare Enterprise (IHE) was formed. The IHE effort has helped to delineate how portions of the DICOM standard can be implemented in practice, so that the necessary common framework for information interchange can be developed in a coordinated and timely manner.

There is particular interest in DICOM compliance from vendors who provide mammographic CAD systems. These systems accept digital image input data, typically scanned from X-ray films, and perform various algorithmic operations on the images obtained in order to help automate the identification of lesions and other structural abnormalities within the breast tissue. Some examples of mammography CAD systems are described in U.S. Pat. No. 5,729,620 entitled "Computer-Aided Diagnosis System and Method" to Wang, and U.S. Pat. No. 6,650,766 entitled "Method For Combining Automated Detections From Medical Images With Observed Detections Of A Human Interpreter" to Rogers et al. DICOM compliance for CAD systems should provide system compatibility, and also support the overall CAD processing workflow.

Digital mammography CAD systems are gaining increasing acceptance and capable digital display and image assessment techniques are continually being developed. As part of this process, there are corresponding changes to conventional techniques and practices for mammography. One area of digital mammography system architects is to provide a workflow schema and support tools that allow practitioners to take more complete advantage of digital display and diagnosis capabilities. In making the transition from display film to display screen, for example, radiologists have certain expectations and behavior patterns that work best for them and that help to systematize their work for efficiency and effectiveness. One of the design challenges is to allow a smooth transition to digital imaging, without compromising the efficiency of existing, familiar methods and to make new capabilities easier to use.

There has been interest in providing a user interface and utilities that are suited for diagnostic imaging. The following references provide some examples.

U.S. Pat. No. 6,734,880 entitled "User Interface for a Medical Informatics System" to Chang et al. describes use of a screen layout for image browsing modeled after that traditionally used for analog film imaging, with added pan and zoom features.

U.S. Pat. No. 6,925,200 entitled "Graphical User Interface for Display of Anatomical Information" to Wood et al. describes an X-ray imaging apparatus with a display screen that provides various arrangements along with different types of markers for identifying specific regions of interest.

U.S. Pat. No. 5,987,345 entitled "Method and System for Displaying Medical Images" to Engelmann et al. describes an image display system that can have multiple terminals for control and display purposes.

U.S. Patent Published Application No. 2004/0102689 entitled "Workflow for Computer Aided Detection" by Metz et al. describes a workflow arrangement associated with the DICOM imaging architecture.

U.S. Patent Published Application No. 2003/0026503 entitled "Workstation Interface for Use in Digital Mammography and Associated Methods" by Kallergi et al. describes a user interface having tools for specifying CAD processing operations and viewing results.

U.S. Pat. No. 6,970,587 entitled "Use of Computer-Aided Detection System Outputs in Clinical Practice" to Rogers et al. describes CAD processing techniques for applying masks, determining thresholds, and performing other imaging operations for mammography systems.

U.S. Patent Published Application No. 2004/0247166 entitled "Method, System and Computer Readable Medium for an Intelligent Search Workstation for Computer Assisted Interpretation of Medical Images" by Giger et al. describes automated utilities for assessing mammography images and classifying abnormal structures in these images.

U.S. Patent Published Application No. 2004/0122790 entitled "Computer-Assisted Data Processing System and Method Incorporating Automated Learning" by Walker et al. describes a method for improving results from computer-assisted diagnostic imaging algorithms using feedback from medical professionals.

While the references listed above provide some measure of support for diagnostic workflow, there is considerable room for improvement.

One challenge recognized by Applicants relates to adapting digital display technology to familiar tools and practices used by the diagnostician. That is, display utilities should conform to existing practices and procedures where possible, rather than forcing a user to adapt to a new diagnostic workflow in order to suit the design of the display system. Traditionally, diagnosticians are used to handling film images and have developed expertise for maximizing accuracy from reading these analog images. Where there are new tools and capabilities with digital imaging systems for Computer-Aided Diagnostics, these should be integrated with familiar patterns of operation where possible. The workflow for a digital diagnostic system should emulate the workflow that is currently used for assessing analog films.

Other challenges relate to the need to correlate information obtained from different medical imaging modalities, including not only x-ray images, but also images from magnetic resonance (MR) systems, ultrasound apparatus, and other medical imaging devices. Inconsistent image processing and display techniques used for these different technologies make it difficult for the diagnostician to use their combined results effectively.

Thus, there is a need for a display platform that supports physician workflow for digital mammography and other medical imaging modalities, that provides improved consistency for correlation of images obtained from different sources and at different times, and that takes advantage of digital capabilities to provide high-resolution image display having suitable image quality for improving the effectiveness of screening and diagnosis.

SUMMARY OF THE INVENTION

An object of the present invention is to provide a method that support diagnostic workflow used in mammography and other imaging disciplines.

Another object of the present invention is to provide such a method that helps to simplify image assessment for users of diagnostic imaging systems.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for supporting diagnostic workflow from a medical imaging apparatus. The method comprises the steps of: a) obtaining a set of at least two images of a patient; b) displaying the set of images according to a user-specified image display layout selected from a plurality of image display layouts; c) associating one or more markers with one or more of the at least two images, each marker identifying a region of interest in the displayed image; d) generating a list of regions of interest having an entry for each marker associated in step c); and e) assigning a classification to each entry in the list according to possible health risk.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

Figure 1:
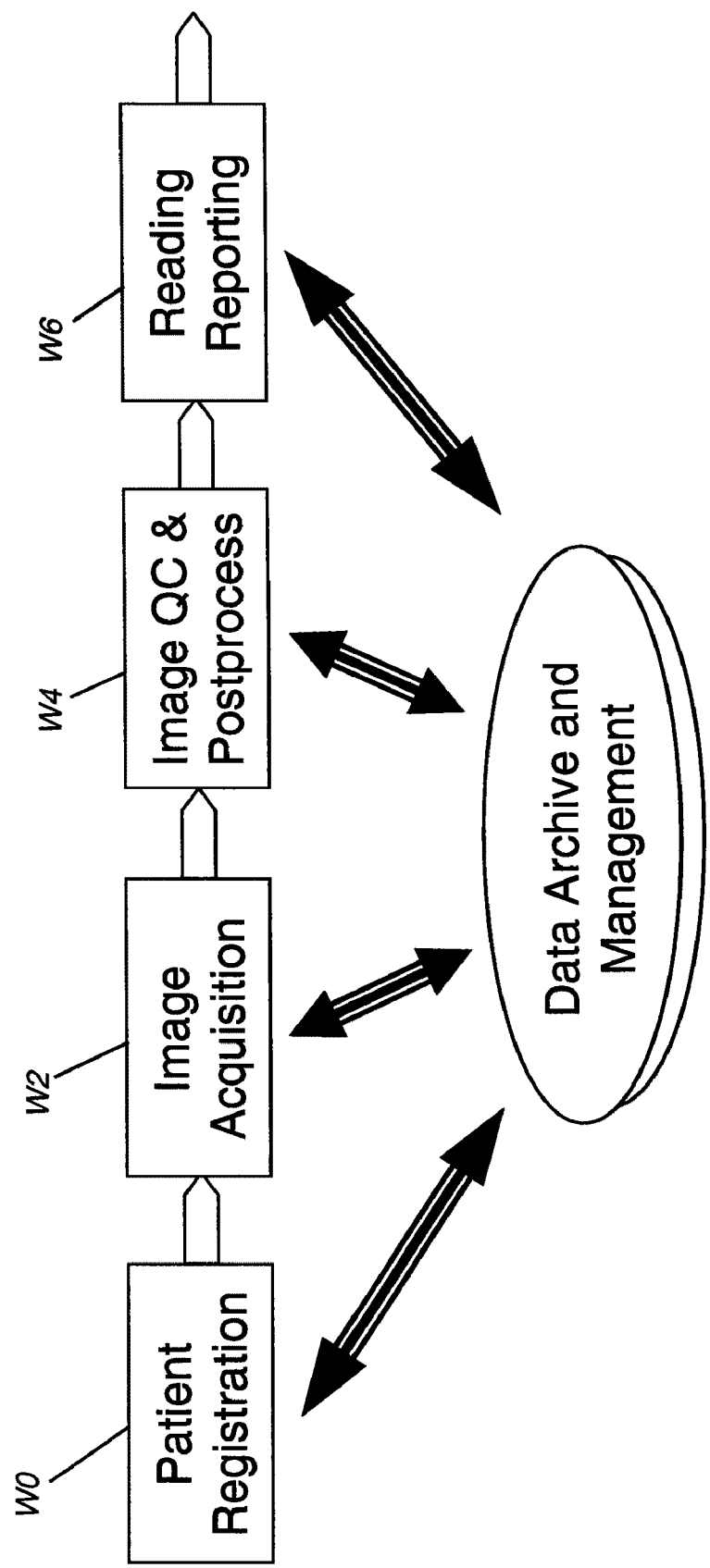
FIG. 1 is a flow diagram showing the basic stages of workflow in diagnostic imaging with CAD systems.

The following is a detailed description of the preferred embodiments of the invention, reference being made to the drawings in which the same reference numerals identify the same elements of structure in each of the several figures.

The present description is directed in particular to elements forming part of, or cooperating more directly with, apparatus in accordance with the invention. It is to be understood that elements not specifically shown or described may take various forms well known to those skilled in the art.

The present invention provides software to aid the diagnostician when displaying and examining medical images for detection, diagnosis, and treatment. The software is designed to conform to the existing workflow patterns of the radiologist or other specialist and to add tools that are helpful for improving efficiency and diagnostic accuracy. For example, features that improve image presentation format and overall image quality, and tools that use non-image data more effectively.

The apparatus and method of the present invention employs a DICOM communications network environment having various types of systems at different levels of conformance to the DICOM standard. To maintain communications and managed CAD workflow within such a system, an Adapter Service can be provided, as described in commonly assigned application U.S. Ser. No. 11/440,978, entitled "DICOM ADAPTER SERVICE FOR CAD SYSTEM" by Heffeman and Zhang, filed on common date herewith and incorporated herein in its entirety by reference. The Adapter Service acts as a type of gateway, data conditioner, and "traffic coordinator" that handles protocol transactions between systems and data transfer to and from storage and peripheral devices. Its infrastructure allows the Adapter Service to be configured for both short-term legacy systems support of proprietary and legacy DICOM systems and longer-term IHE-compliant systems support, at varying levels of compliance.

The block diagram of FIG. 1 shows, for DICOM-compliant systems, the basic, high-level workflow sequence for diagnostic imaging using CAD. A patient registration step W0 sets up data structures for processing the digital images to be obtained for the patient. In an image acquisition step W2, digital images are obtained in any of the suitable medical imaging modalities, such as those described subsequently. An image quality control and postprocessing step W4 is executed, first to check on the validity of the image data itself, then to perform the CAD post-processing functions for screening and diagnosis. A final reading and reporting step W6 stores and displays processed results for analysis and patient assessment by the diagnostician. These processes interact with data archival and management tools for obtaining, storing, and controlling access to patient images.

Figure 2:
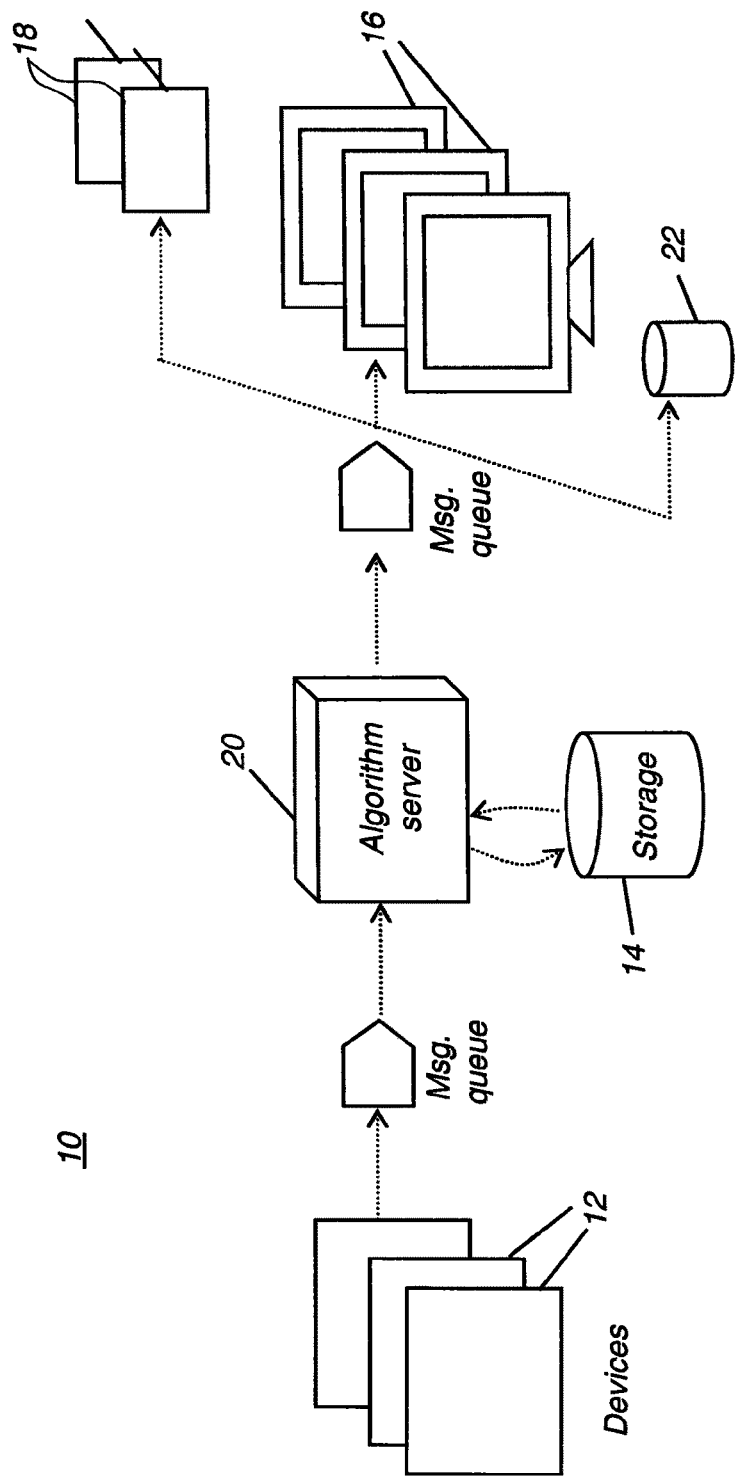
FIG. 2 is a block diagram of a CAD system having interfaces to multiple input and output peripherals, as anticipated in the DICOM model.

The block diagram of FIG. 2 shows an exemplary mammography CAD system 10 using image data, for one or more medical imaging modalities, that can be obtained from a range of different sources and with multiple image capture devices 12. As noted earlier, there are a plurality of available medical imaging modalities for medical diagnostic and imaging systems. Examples include, but are not limited to, computed tomography (CT) systems, x-ray systems (including both conventional and digital or digitized imaging systems, including computed radiography (CR)), magnetic resonance (MR) systems, positron emission tomography (PET) systems, ultrasound systems, and nuclear medicine systems. These medical imaging modalities can complement each other and offer a diagnostician a range of imaging techniques for particular types of tissue, organs, physiological systems, and the like. Health care facilities can use several such imaging systems of different imaging modalities at one or more sites.

Images can be scanned from film in current environments, or can be generated from digital sources of various types, with the images varying in resolution, dynamic range, and other characteristics and accompanied by variable amounts of patient metadata. Disparity in image attributes between different medical imaging modalities has made it difficult, in some cases, to correlate and use image data effectively. As is shown in a subsequent description, the display system of the present invention can be employed with multiple medical imaging modalities and provide tools and techniques to use results from different systems in a cooperative manner.

Still referring to FIG. 2, generally, the output from an algorithm server 20 is made available for use by a PACS (Picture Archiving and Communications System). CAD system output is configured for presentation, such as on a display 16, or in printed form from a printer 18, and/or can be stored on an internal or external storage device 14 or 22 or on a removable storage medium for possible future use. The storage device is preferably adapted for use on a range of different equipment.

Figure 3:
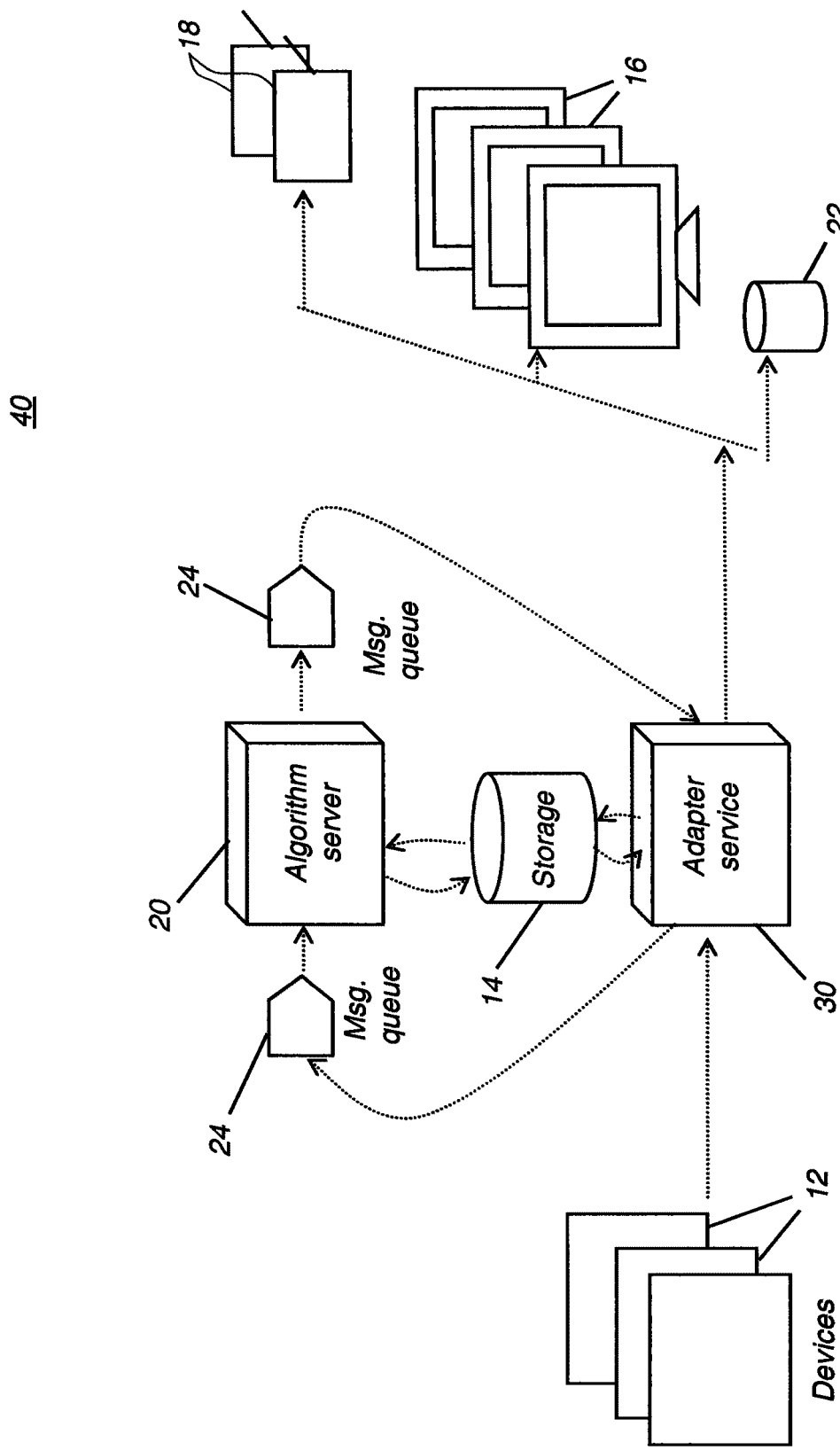
FIG. 3 is a block diagram of a CAD system having an adapter service according to embodiments of the present invention.

Referring now to the block diagram of FIG. 3, there is shown a CAD apparatus 40 in which an adapter service 30 supports algorithm server 20. Adapter service 30 provides a means to obtain image data from multiple image capture devices 12 and to manage the workflow in which files are provided to, and received from, algorithm server 20. Adapter service 30 is configurable and can support multiple data interchange protocols, both for IHE-compliant DICOM interaction and for legacy system interface with input, output, and storage components.

Adapter service 30 supports a number of types of data sources as image capture devices 12 for obtaining patient data files, such as digitized mammography film, for example. Proprietary system image data may be provided as digitized data from film, in a particular file format, such as TIFF (Tagged Image File Format). To obtain the image data from the sending image capture device 12, adapter service 30 maintains a communication process with the sending system. In one embodiment, characteristic of proprietary system and legacy DICOM environments, image data files are automatically sent, or "pushed" to the network address of the adapter service 30 computer platform. In other embodiments, more characteristic of the IHE-compliant system, a general-purpose work-list service is used to coordinate file transfer. Adapter service 30 utilizes storage device 14 of CAD apparatus 40 for storage of the received input image data.

When adapter service 30 has received and stored the input image data from any of image capture devices 12, algorithm server 20 is updated accordingly, such as by using a message queue 24. In one embodiment, message queue 24 is implemented using a Windows MSMQ (Microsoft Message Queue) message utility. Algorithm server 20 responds, in turn, by obtaining the image data from storage device 14 and operating upon the data to provide content for a structured report (SR) or other suitable data object containing the CAD contribution. Adapter service 30 is informed of status and progress, for example, by message queue 24. The generated content from CAD analysis can then be stored at storage device 14 and can be provided to the various output systems, including display systems, as was described with reference to FIG. 2.

Display System Relative to FIGS. 2 and 3, the apparatus and methods of the present invention support the diagnostic identification, display, and reporting functions of CAD output display 16 for improved diagnostic screening of mammography and other types of medical images. Implementation of the various processing capabilities described subsequently can occur as directed by algorithm server 20 or by adapter service 30. Optionally, a separate computer or logic processing unit can be used to provide the functions of the display system.

Figure 4:
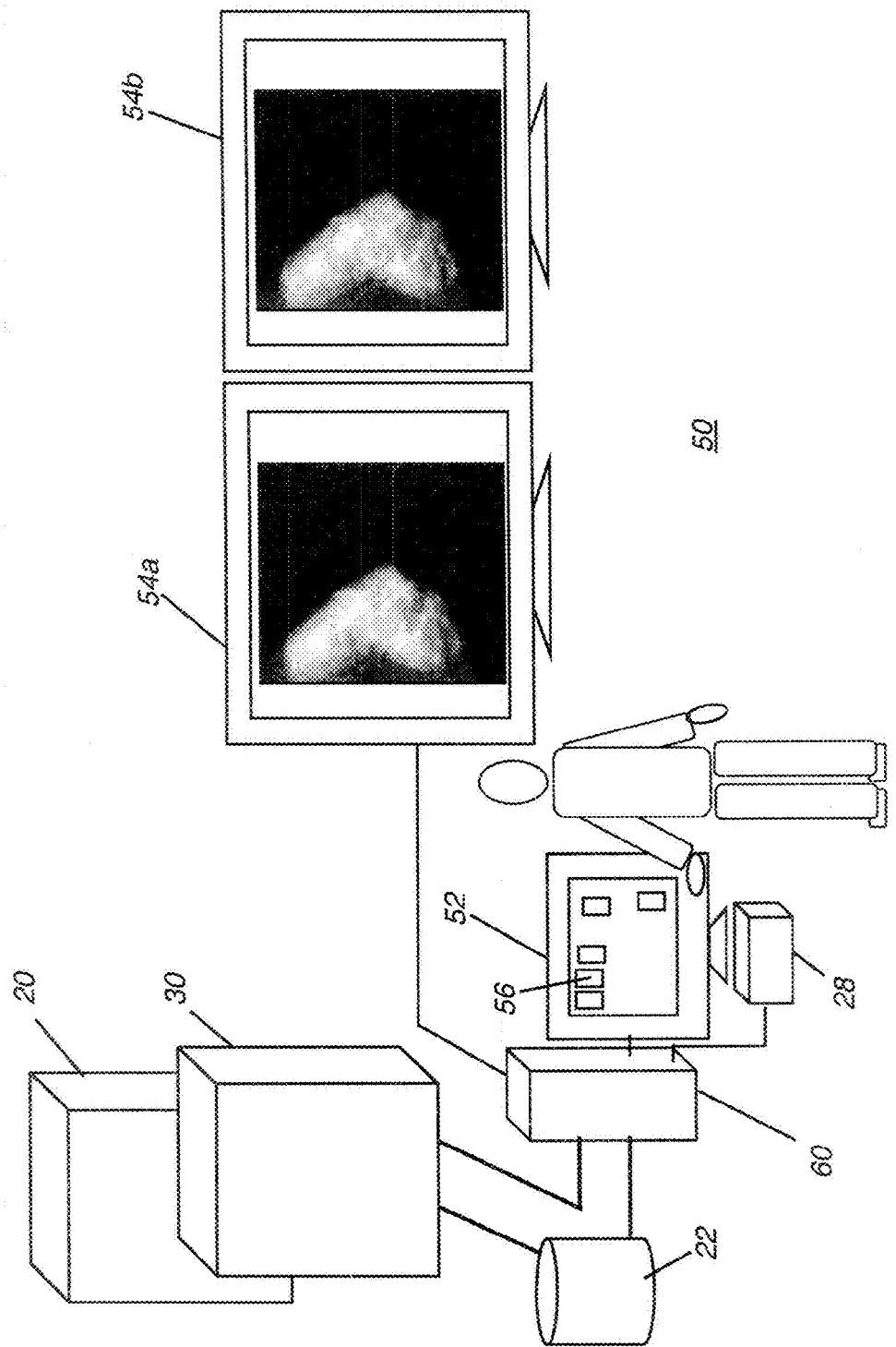
FIG. 4 is a block diagram showing major components of a display system for diagnostic imaging.

Referring to FIG. 4, there is shown a display system 50 for diagnostic imaging in one embodiment. Relative to the DICOM/IHE compliant arrangement of FIGS. 2 and 3, display system 50 can supplement or substitute for display 16 of CAD apparatus 40. It is noted, however, that display system 50 of the present invention is not intended to be a "one-way" display system that shows results of processing performed at other equipment, but can be interactive with CAD apparatus 40, with data transferred both to and from CAD apparatus 40. Operator commands and actions performed at display system 50 can impact the operation of algorithm server 20 or adapter service 30 and generate response activity, and can modify the information that is stored by adapter service 30 for a specific patient.

Display system 50 includes a navigation monitor 52 and one or more high-resolution display monitors 54a, 54b. Navigation monitor 52 allows operator interaction, accepting operator commands for various display arrangements and allowing the operator to select an optimal/preferred format for display. In one embodiment, navigation monitor 52 is a color monitor at a suitable resolution for computer monitors, such as 1600×1200 (so-called Ultra Extended Graphics Array or UXGA) resolution, for example. For navigation monitor 52, color display capability is preferred for its particular utility for image and data presentation. Images displayed on navigation monitor 52 are reduced-size or thumbnail reference images 56, such as can be formed from high-resolution images by appropriate sampling techniques well known to those skilled in the imaging arts. This arrangement, using navigation monitor 52 for thumbnail display and for image manipulation, allows the full display surface of high-resolution display monitor 54a or 54b to be used as a display area for diagnostic image display, without a requirement to use any portion of the display screen itself for control or command entry functions.

A command entry apparatus 28 is employed for entry of operator instructions that would be used, for example, to identify a case for display and to specify which images for a patient to display in the display areas of high resolution display monitors 54a and 54b. Command entry apparatus 28 can include a keyboard, mouse, or pointer, for example, or can also or alternately include a voice recognition apparatus for interpreting vocal instructions from the physician and operating in response to those instructions. This can allow "hands-free" operation and permit the diagnosing physician to concentrate on the images displayed rather than on the manipulation of conventional mouse and screen navigation tools.

High-resolution display monitors 54a and 54b are typically monochrome, at very high resolution. In one embodiment, for example, display hardware having resolution of 5 megapixels or better are employed for display monitors 54a and 54b. Monitors 54a and 54b are to have suitable resolution for screening diagnosis. Since navigation monitor 52 is provided for thumbnail image 56 display and image selection and management, high-resolution monitors display monitors 54a and 54b are freed from the requirement to display control screens and other mechanisms that may be used to enter commands, but do not require high resolution portrayal. The operator preferably arranges the images and specifies their format using the lower resolution navigation monitor 52 and entering instructions at command entry apparatus 28. Alternatively, it may be useful to provide some subset of command or control functions at display monitors 54a and 54b, such as using touchscreen overlays or by supplying other operator interface tools for these devices. However, a feature of having navigation monitor 52 separate from display monitors 54a and 54b is to segregate control and display functions, such that the high-resolution digital display meets or exceeds the imaging accuracy currently available using film or other analog imaging output.

Workstation 60 is optional and its function can be performed by another apparatus. For example, navigation monitor 52 and its associated display monitors 54a and 54b can be connected directly to adapter service 30 or to algorithm server 20 in other embodiments.

Enhancing Diagnostic Accuracy The present invention provides enhanced diagnostic accuracy. Metadata about the patient can be displayed on navigation monitor 52 (or optionally on display monitors 54a, 54b) along with image data. This metadata can also be used by algorithm server 20 (FIGS. 2 and 3) in executing the CAD processing and analysis routines. Factors such as family history, personal health and procedures history, physical examination findings, and age can be employed as part of the software that evaluates imaged data and can impact its display.

Attributes of breast composition or breast tissue density can affect the accuracy of diagnostic software. In the present invention, the American College of Radiology (ACR) Breast Imaging Reporting and Data System (BI-RADS) reporting nomenclature and data formatting is preferably employed to indicate tissue density and other appropriate factors, using data obtained from the digital image. This provides a standardized assessment of attenuating tissues of the breast to help indicate the relative likelihood that a lesion is hidden by otherwise normal tissue for a particular patient. This attribute can also be used to modify image contrast provided by the system. Pattern-1, Pattern-2, Pattern-3, or Pattern-4 breast density descriptions, as defined by BI-RADS, an assist to quantify differences in tissue attributes between patients. These values can be automatically determined in image analysis at algorithm server 20, but can be subject to review by the diagnostician and may be editable.

Figure 5:
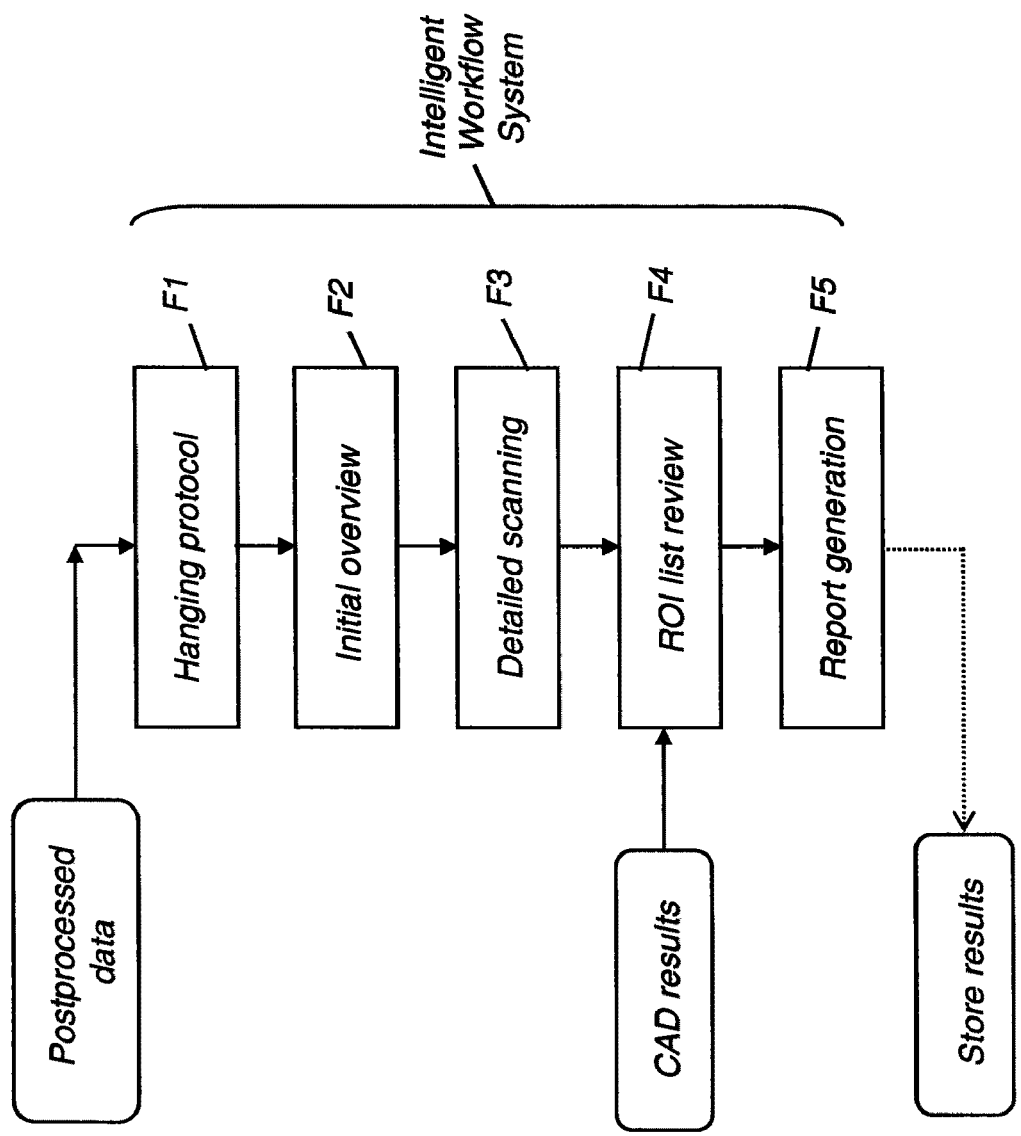
FIG. 5 is a block diagram showing the workflow sequence of the present invention.

Intelligent Workflow System Referring to FIG. 5, there is shown a flow sequence for workflow steps using the method and apparatus of the present invention. Initially, post-processed data from image acquisition apparatus (in image acquisition step W2 in FIG. 1) serves as input to the workflow. When the patient case is identified, an operation in this workflow involves selection of a preferred display layout arrangement or image hanging protocol in a hanging protocol selection step F1. This layout arrangement or hanging protocol defines how the set containing two or more patient images is to be displayed.

Figure 6A:
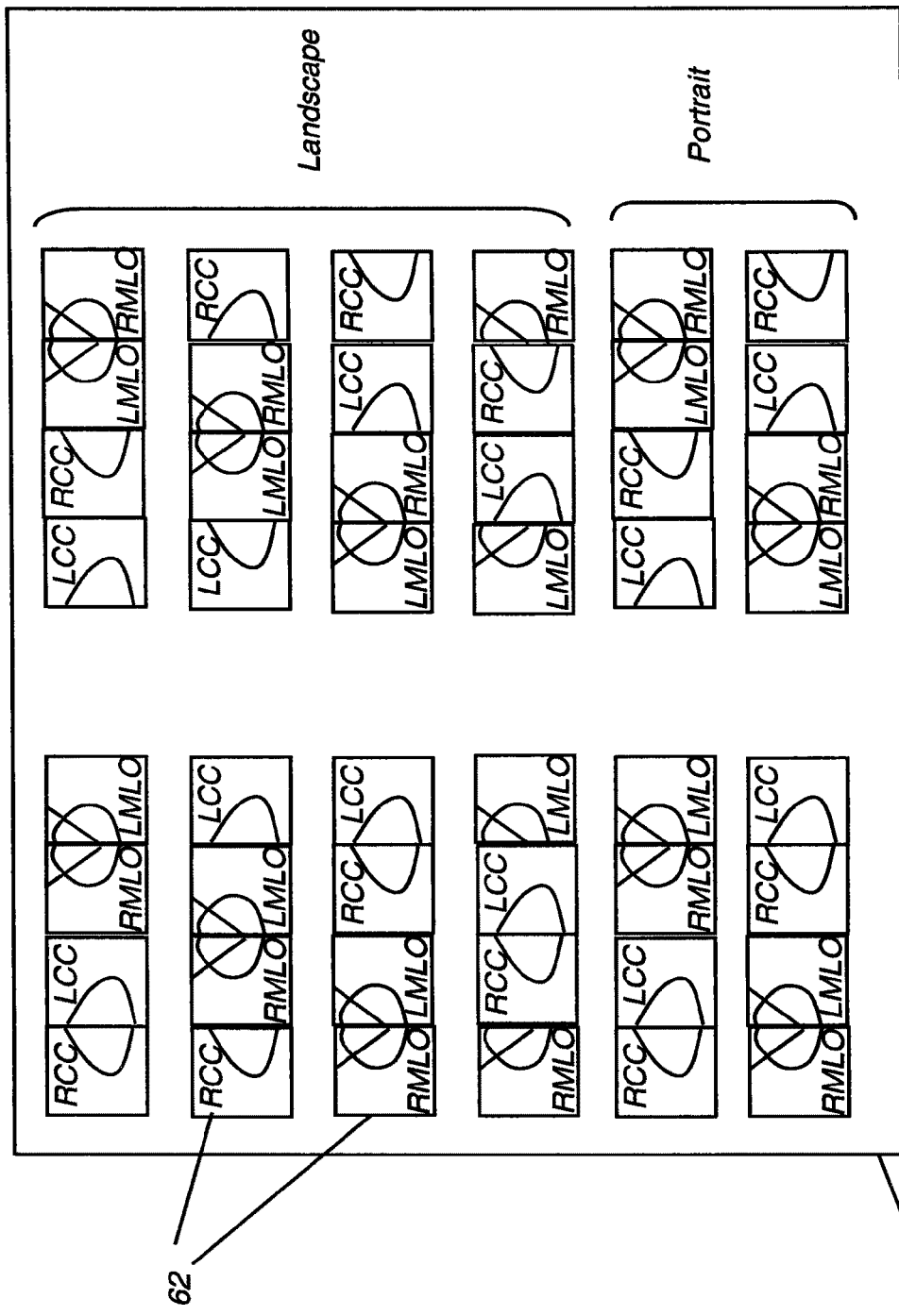
FIG. 6A is a plan view showing various arrangements of images that can be selected as suitable image hanging protocols.

In x-ray mammography, typically, two views are taken of each breast, along cranio-caudal (CC) and mediolateral oblique (MLO) planes. This yields a set containing Left and Right cranio-caudal (LCC, RCC) and Left and Right mediolateral oblique (LMLO, RMLO) views. The plan view of FIG. 6A shows a plurality of candidate hanging protocol arrangements that can be specified for the set of these four views 62 for a patient, both for the current exam and for a previous exam.

In display system 50 of FIG. 4, thumbnail views 62 appear for selection on navigation monitor 52. The operator specifies the desired imaging hanging protocol by a command entry, such as using a touchscreen, a keyboard command, verbal instruction, or employing a cursor control mechanism. The selected views then display on high resolution display monitors 54a, 54b.

Figure 6B:
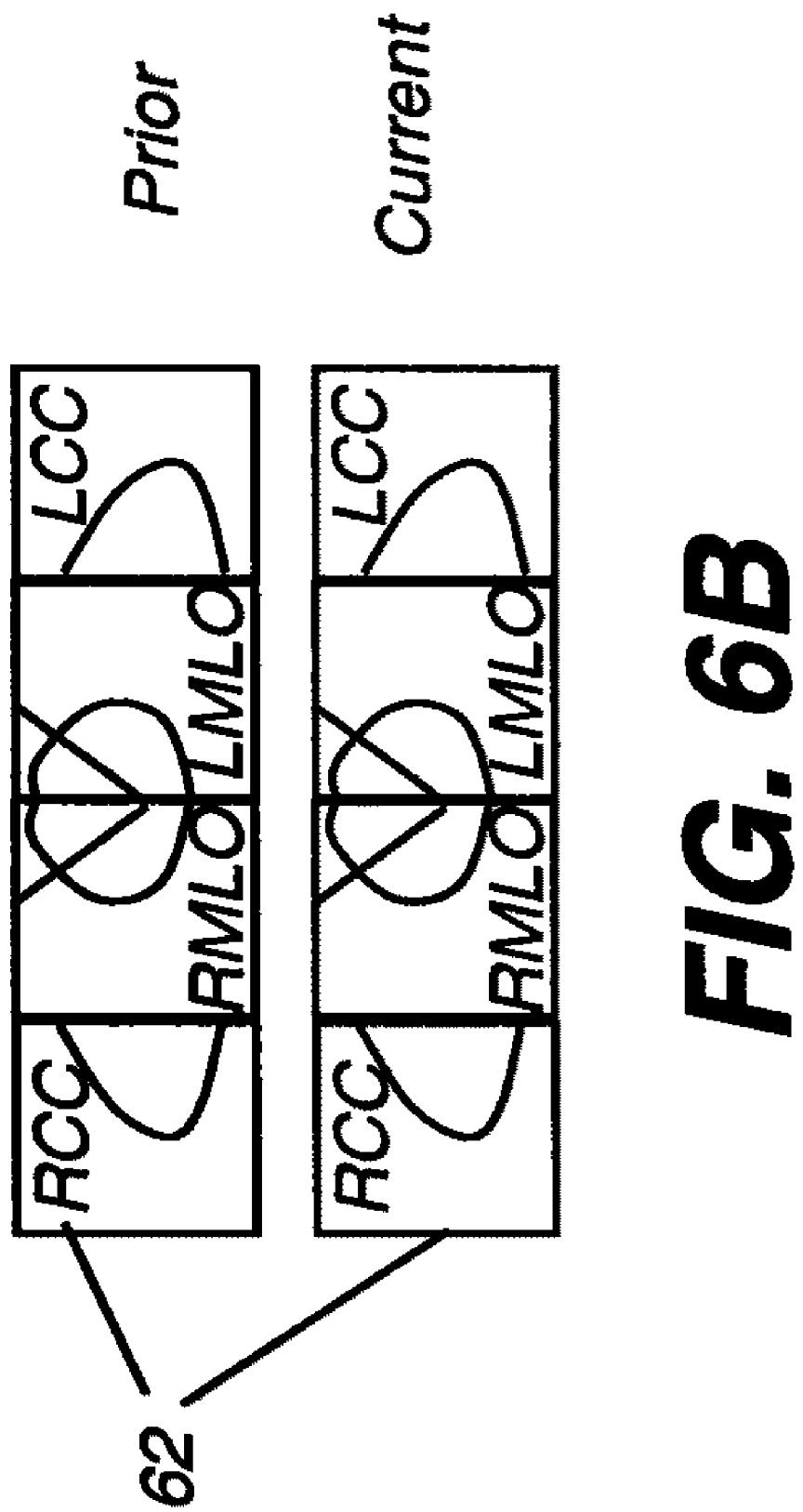
FIG. 6B is a plan view showing one of a possible number of alternate arrangements for simultaneous display of current and prior exam results.

In the alternate embodiment of FIG. 6B, the user can select from a hanging protocol that positions images from the current exam along with a set of images from an earlier exam, with images arranged suitably for one-to-one comparison. The system responds by automatically displaying the mammography images according to the selected protocol. Both landscape and portrait arrangements can be used, as is shown in the examples of FIG. 6A. It is noted that only one example is shown in FIG. 6B, and any suitable arrangement of the mammography images can be used.

Figure 7:
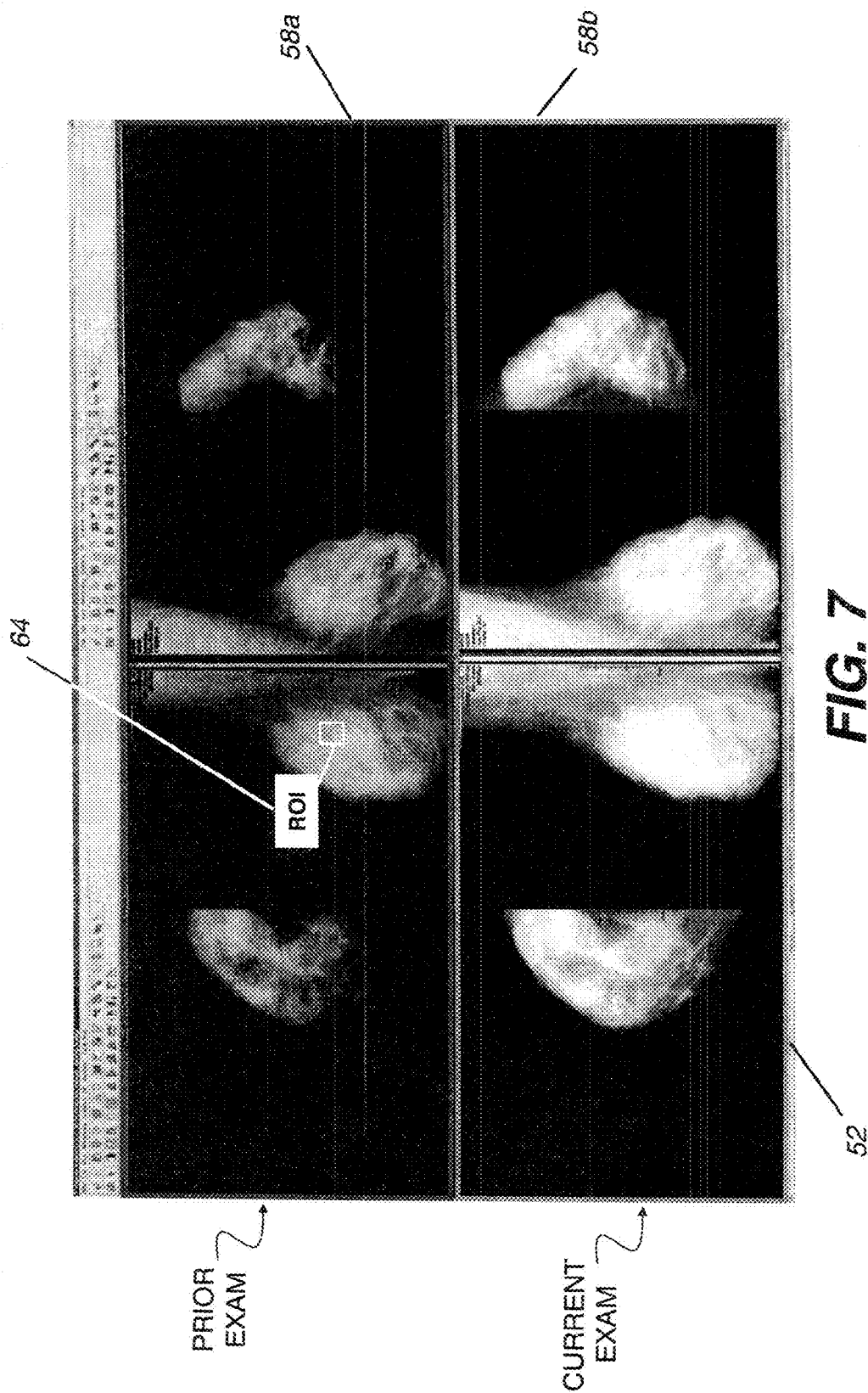
FIG. 7 shows displayed images arranged on-screen according to one selected image hanging protocol, with borders highlighting current and prior exam results.

FIG. 7 shows one of the candidate hanging protocol arrangements with images from prior and current exams. Where suitable, image contrast, sizing, and position can be adjusted automatically to make current exam results and prior exam results comparable for diagnostic assessment. Images from the prior exam can be from any earlier imaging session, preferably with an interval between exams of one day or longer.

Sizing and scaling can automatically be provided for the specified images in the desired hanging protocol. The system automatically calculates the image size and location according to the selected protocol. The system also calculates an appropriate contrast window-level for display. Breast mask information, available from the CAD system as part of the preprocessed data, can be used to optimize image contrast for best display.

For the displayed images, pan and zoom utilities can be available, according to commands entered at navigation display 52. As other display alternatives, single image enlargement is also available, as shown in the example of FIG. 4, where display monitors 54a and 54b each show the same view on the full screen, one for each of current and prior exams. Single image enlargement may be performed, for example, upon verbal command or by clicking on the image displayed at navigation display 52. This mode can be toggled back to the original display mode or another image can be selected using navigation display 52.

Adjustment for breast implants can also be provided, in order to improve diagnostic accuracy where implants have been used. For patients having implants, typically 8 mammography views are obtained. Four additional views are obtained using special tissue displacement techniques, since the implant material is highly opaque, and the physical presence of the implant compresses fat and glandular tissues, creating more homogeneous dense tissue that frequently lacks the contrast needed to detect subtle early features associated with breast cancer. The additional four displaced images may be used in a hanging protocol, similar to that described for the standard four-image set. As with the standard sets of images, the displaced images from a current mammography session can also be displayed with corresponding displaced images from a prior session, with suitable contrast adjustment and registration utilities. Where appropriate, implant displaced views can be toggled in view ports on the display screen and correlated with earlier results, so that display of a specific view (standard or displaced mammography) automatically causes the corresponding prior exam view to be displayed.

Once the hanging protocol is specified and images displayed on high-resolution display monitors 54a and 54b, various supplemental utilities are provided in order to optimize the usability of the displayed images for an initial overview step F2. Referring to the plan view of FIG. 7, color coding can be used in order to facilitate comparison of earlier with later images. In the embodiment shown, a color outline or border 58a or 58b is applied around images from prior and current exams. Color border 58a or 58b can be formed around the high-resolution images themselves; however, in the embodiment shown in FIGS. 4 and 7, high-resolution display monitors 54a, 54b are monochrome; thus, color border 58a or 58b is used only at navigation monitor 52. Alternately, some other type of border pattern could be applied around prior or current exam images at monochrome display monitor 54a, 54b, such as a hatched pattern or other suitable marking. In image processing, a prior image can be used as a baseline for assessment of changes.

Alternately, color coding can be used to identify the type of image. As described earlier, the system of the present invention can display images from multiple medical imaging modalities, including x-ray, ultrasound, and other image types. It may be useful to outline images using color to indicate different image sources as well as, or in addition to, different exam sessions.

Image contrast is a an attribute for providing a display image that can be accurately assessed. An automated image contrast adjustment can be made using breast mask knowledge to eliminate image noise, as described in commonly assigned application U.S. Ser. No. 11/285,231, entitled "AUTOMATIC IMAGE CONTRAST IN COMPUTER-AIDED DIAGNOSIS" by Zhang et al., filed on Nov. 22, 2005, based on Provisional Patent Application No. 60/631, 156, filed on Nov. 24, 2004, and incorporated herein by reference. Image contrast adjustment is used for both current and prior exam results in one embodiment, thus helping to standardize the image presentation so that changes between earlier and later image data can be more readily visible. Contrast adjustment can also be provided for images obtained in different medical imaging modalities. Image size can also be computed and adjusted automatically, in order to suit the dimensional requirements imposed by display apparatus.

Patient metadata can be displayed concurrently with the images, on either or both display monitors 54a, 54b and navigation monitor 52. This metadata can include, for example, patient age, applicable family history, medical history, physical examination findings, and other appropriate data for reference by the diagnosing physician. It is noted that patient data can be used by CAD system algorithms for providing information that assists in detection and assessment procedures. Thus, in addition to being available to the viewer when reviewing displayed images, patient-specific information can serve to improve the automated diagnosis capabilities of the CAD system.

Features available from system software to support this initial workflow step include automatic assessment of breast density or overall breast composition using BI-RADS descriptors, as noted earlier. BI-RADS descriptions used are the following in one embodiment:

Pattern-1: Breast almost entirely fat (<25% glandular).
Pattern-2: Breast tissue exhibits scattered fibroglandular densities (approximately 25-50% glandular).
Pattern-3: Breast tissue is heterogeneously dense, which can obscure detection of small masses (approximately 51-75% glandular).
Pattern-4: Breast tissue is extremely dense, which may lower the sensitivity of mammography (>75% glandular).

These can be computed as part of the preprocessed data from the CAD system and can be subject to confirmation or correction by the radiologist or other diagnostician.

During initial overview step F2, a tag operation is available to the diagnostician for associating a tag or other marker to a region of interest (ROI). Using this capability, the attending radiologist can identify one or more ROIs and begin to assemble a Tag List used for more detailed analysis and assessment. For example, FIG. 7 shows a tag 64 that has been applied to a particular abnormality in the prior exam image. Tag 64 displays on both navigation monitor 52 and can also be displayed on any high resolution display on high-resolution display monitor 54a, 54b. ROI tagging can be performed in either of two review modes during initial overview step F2:

(i) during an overview of all of the images in a study, so that the diagnostician can mark all "obvious" ROIs; and (ii) during an overview of an enlarged image, so that the diagnostician can mark any detected ROIs that are more subtle.

The entered command for placing an ROI tag on an image can be entered in a number of ways, for example, by including using a verbal command, using a mouse or other type of pointer, or using a touchscreen.

Figure 8:
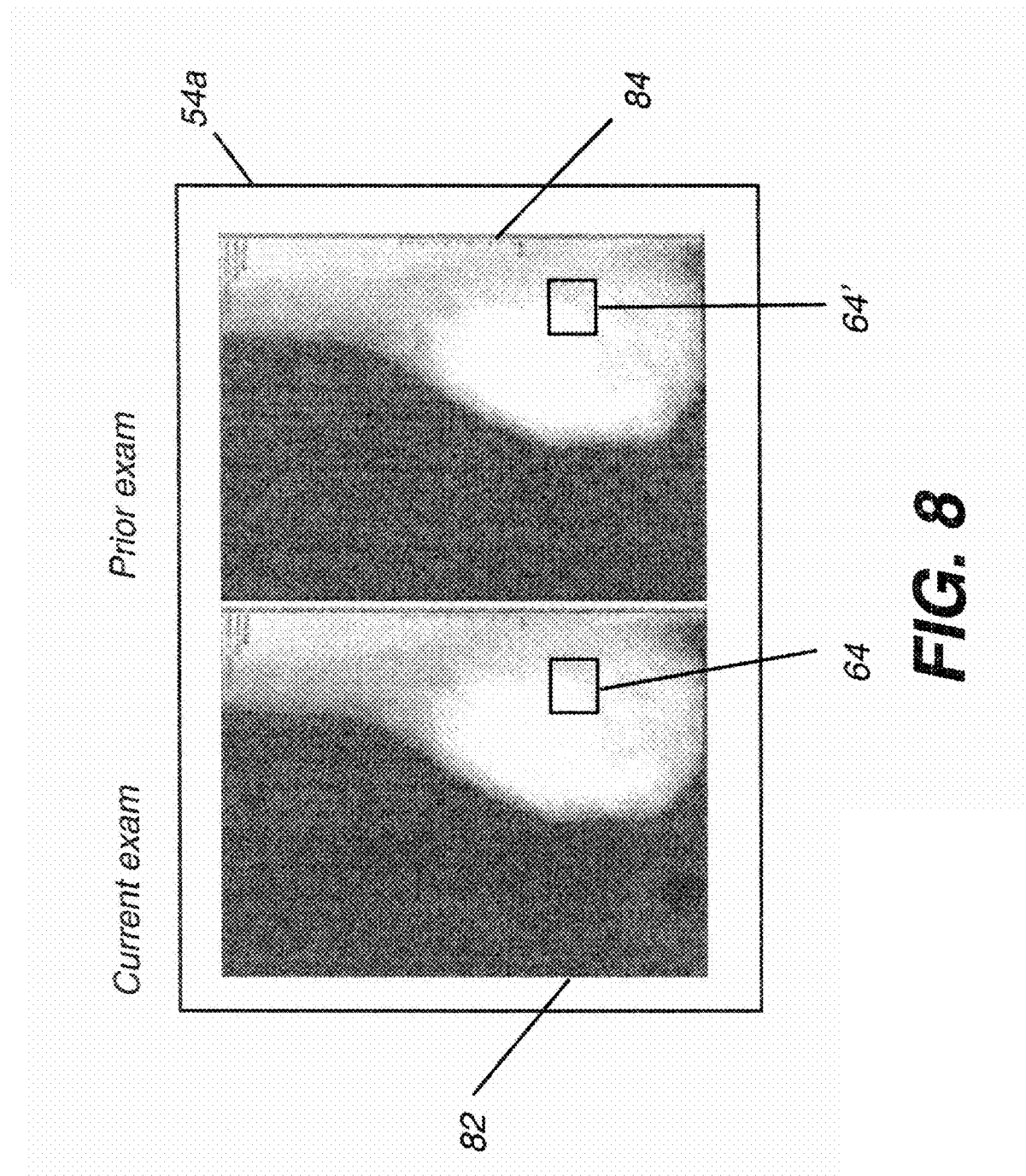
FIG. 8 shows an image display with current and prior exam views for a patient, arranged side by side.

An automatic registration of an ROI to other images can be executed during this step or at a later step in the workflow. As shown in FIG. 8, for tag 64 on a current exam image 82 on display monitor 54a, a corresponding tag 64' can be registered on a prior exam image 84. Image processing executed by CAD software can automatically register tag 64 to its corresponding prior image 84 or, alternately, to an image that is a different view. For example, if the diagnostician identifies an ROI with a tag 64 on a cranio-caudal (CC) view, the CAD software may automatically identify the same area in a mediolateral oblique (MLO) view of the same breast or of the other breast and assign tag 64' appropriately. This feature can require the use of imaging registration algorithms, familiar to those skilled in the image processing arts. Registration can include scaling functions as well as vertical or horizontal alignment of tissue structures, for example.

Spatial registration of images themselves, with or without ROI tags, can be useful for improving diagnostic accuracy. System 50 of the present invention can use image processing techniques to register similar views for a patient, whether the views are prior and current exam images for the same breast or are lateral right- and left-views for a patient from the same exam session. FIG. 8 shows spatial registration of comparable views, such as might appear on display monitor 54a, 54b or on reduced size on navigation monitor 52. Registration can include both scale adjustment and horizontal or vertical alignment of the same tissue structure in multiple images. Spatial registration can also be particularly helpful when displaying images from different medical imaging modalities, such as when displaying x-ray images side-by-side with ultrasound images, for example. Registration can also apply where there is a magnified view of interest and it is advantageous to show the same area of interest from an earlier exam or from an image of a different medical imaging modality. The operator can override default registration where desirable.

Tags 64 can be displayed on the image in various ways. A circular or polygonal icon or pointer may be provided, for example, as an overlay on top of the displayed image, as shown by the example tag 64 in FIG. 8. In one embodiment, touching the screen of navigation monitor 52 in an area is sensed and generates a tag automatically, with tags automatically numbered in sequence. An <escape> key or other "undo" command is used to remove a tag or to disable ROI tagging upon touching the monitor screen or entering a verbal command or other instruction.

Utilities for Detailed Scanning Referring again to the flow diagram of FIG. 5, a detailed review step F3 follows initial overview step F2. System 50 of the present invention provides a number of tools and utilities for supporting this more detailed review for mammography and similar imaging processing.

In conventional visual assessment of film-based mammography x-ray images, a radiologist typically scans the film using a magnifier, scanning in a set pattern, such as moving from left to right and from the top of the display downward. A number of different patterns are used, depending on preferences of the examining physician and depending on the image type. Other scan patterns may follow skin contour or be directed to particular tissue areas and scan in a pattern from that reference point, such as in an ever-widening circular pattern, for example.

Display system 50 of the present invention provides a programmable scanning utility for scanning, or alternately, "panning", the image display as an automated type of "electronic magnifying glass". To emulate the scanning function that is conventionally performed manually, the system of the present invention electronically displays the same type of magnified image and pans the display to provide a scanned view.

Figure 9:
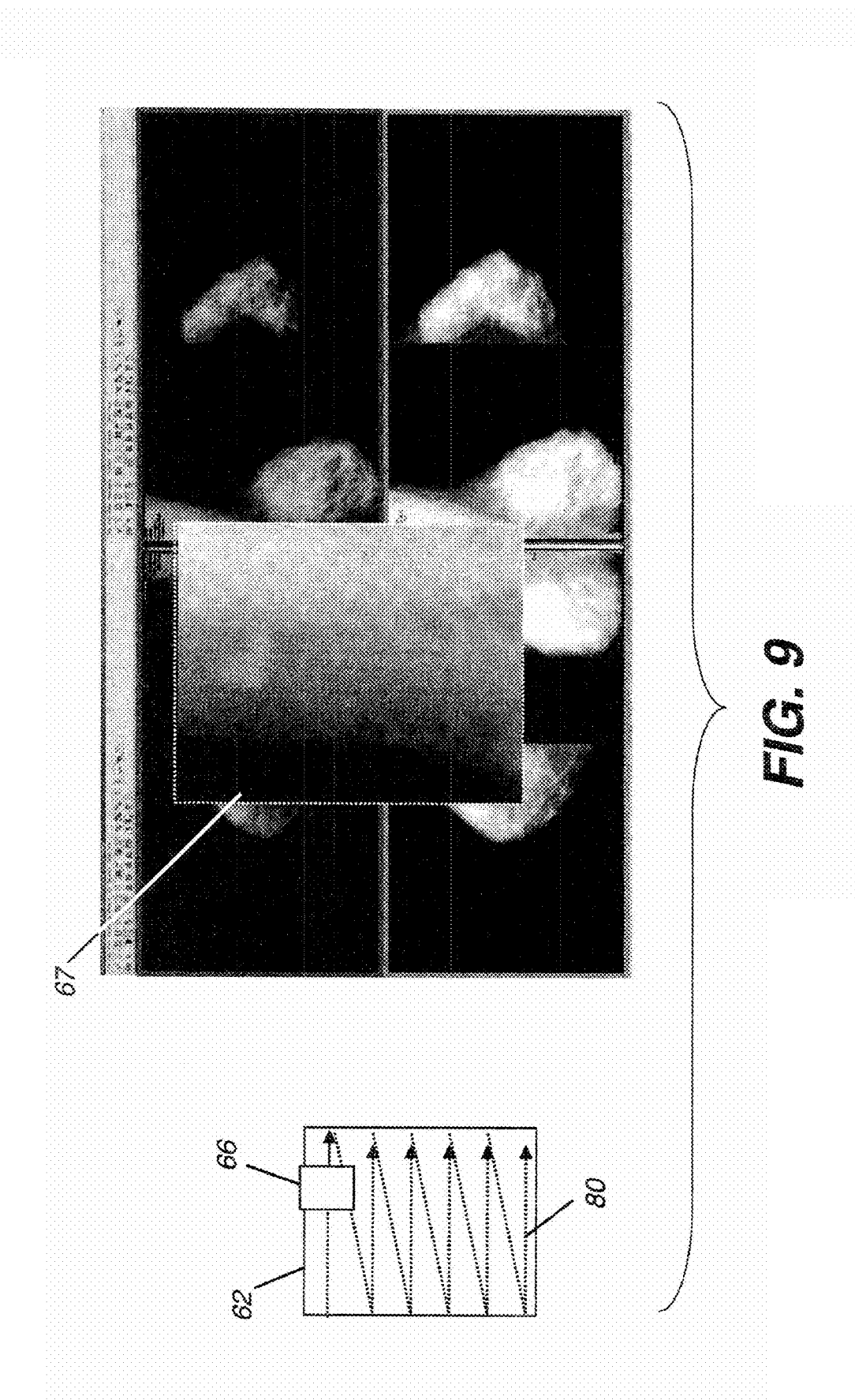
FIG. 9 is a plan view showing magnification windows, with highlighting provided over a region of interest.

Referring to FIG. 9, there is shown an arrangement of views with a magnification outline window 66 and corresponding magnification display window 67. To execute this scanning function, the operator enters an appropriate instruction and positions a magnification outline window 66 on view 62. The operator observes the scanned, magnified portion of the image, in one or more magnification display windows 67, on the display monitor. This provides the "electronic magnifying glass" that pans, that is, scans across, the image automatically, following a selected scan pattern 80, such as that traced in a view 62 of FIG. 9. View 62 can be, for example, one of the diagnostic images displayed. During the scan display, the operator has the option to pause, adjust scanning speed or direction, specify movement increments, pan to change the displayed area, or change magnification or size of the magnification display window 67. The operator can also select a desired scan pattern 80.

The scanning speed can be varied automatically and can be conditioned according to a detected image data characteristic. For example, scanning speed can be automatically slowed down in the vicinity of a detected ROI or where tissue density is above a threshold level. An interactive operator instruction can cause scanning to speed up or slow down appropriately, or to change pattern, reverse direction, stop, restart, or dynamically change image magnification, contrast threshold, or other image characteristics for magnification display window 67. Scanning is continuous in one embodiment; in another embodiment, successive images are a discrete increment apart, rather than continuous in appearance. The operator can enter a save command in order to obtain a "snapshot" of the scan at a certain point, without interrupting the traversal of magnification outline window 66 along view 62. The same pattern 80 or an alternate pattern 80 can be used for different views as well as for views taken at different times.

To execute this function, magnification outline window 66 is defined to be some suitable dimension, smaller than the full-sized diagnostic image (represented by view 62 in FIG. 9). The magnified portion that appears in magnification display window 67 then corresponds to a scaled version of the full image defined by magnification outline window 66. Moving magnification outline window 66 effectively redefines the boundaries of the magnified image that displays. Scan pattern 80 can operate in a "continuous" mode, so that magnification display window 67 appears to move continuously (that is, smoothly) across the display screen. Alternately, scan pattern 80 may change the relative position of magnification outline window 66 in discrete increments, so that, for example, each successive redefined magnified image portion is displaced 8 mm from the previous magnified image portion. The relative movement, speed, size of magnification display window 67, and other variables can be stored with scan pattern 80 or can be entered or edited by the viewer according to viewer preferences or other circumstances.

In one embodiment, scanning pattern 80 can be learned from the operator, such as using a touchscreen on navigation monitor 52, for example. The operator enters a command to put the system in a learning mode, then using a finger, stylus, or other pointer or instruction entry mechanism, traces or otherwise defines a path over some portion of the monitor screen to generate a pattern that can be stored and retrieved for use with images of a specific type. Use of this sequence is shown in the plan view of FIG. 9. Here, for example, view 62 is on navigation monitor 52 as a reduced-size thumbnail, with the thumbnail of magnification outline window 66 traced in position. The enlarged magnification display window 67 appears on display monitor 54a, 54b.

A number of patterns 80, whether provided with the system as defaults or taught to the system in this manner, can be made available to the operator upon command, such as by selection from a menu of available patterns 80. Thus, the system can be customized to scan using techniques that are best suited to the preference of an individual practitioner. Interactive scanning, where magnification outline window 66 is moved across the image by the viewer, is also available in another embodiment. To accomplish this, a touchscreen is used at navigation monitor 52. In response to an appropriate command, magnification outline window 66 appears in outline on view 62, a thumbnail view of the full image. The diagnostician then uses a finger or other stylus to scan magnification outline window 66 across view 62, thus allowing scan pattern 80 to be controlled by the viewer in a real-time manner.

In applying this programmable scanning and magnification utility, the system adapts image contrast for the view displayed within magnification display window 67 to optimize image display for more accurate detection and diagnosis. To accomplish this, the system can apply contrast to magnification display window 67 at a different setting than is applied to the standard, full-sized displayed image.

Figure 10:
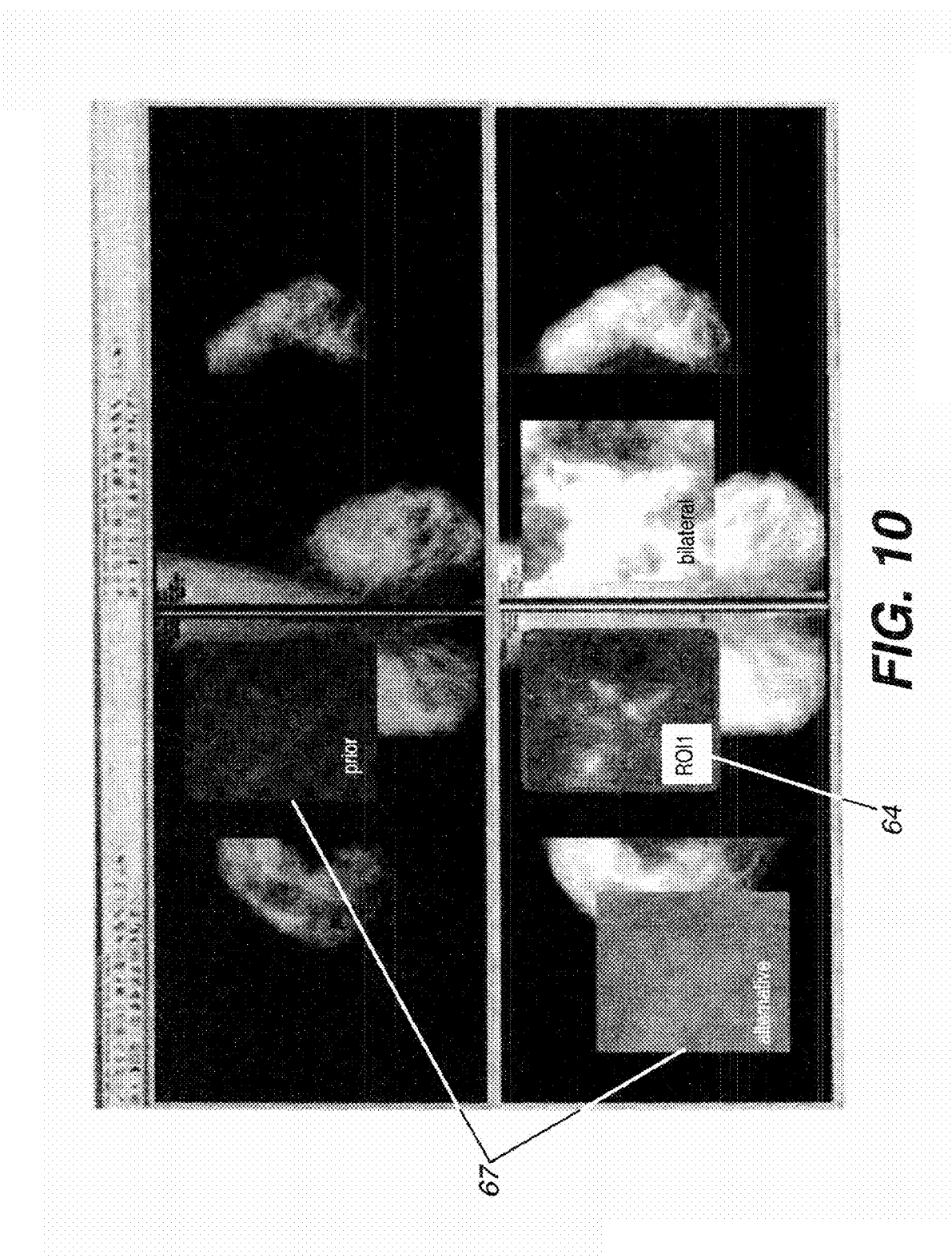
FIG. 10 is a plan view of a screen layout showing multiple magnification windows for a region of interest in different views.
Figure 11:
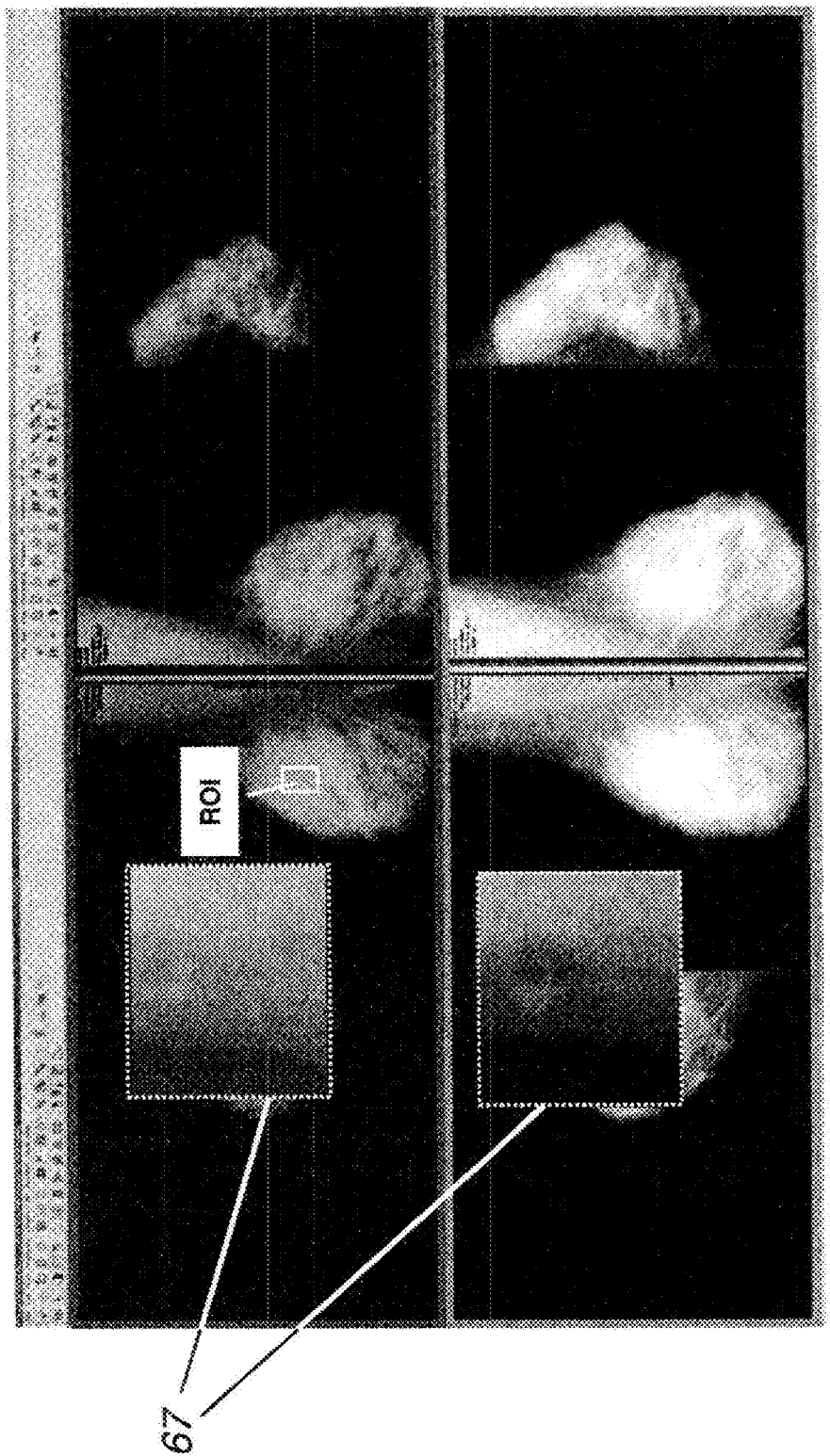
FIG. 11 is a plan view showing magnification windows provided by the display system user interface.

As shown in FIGS. 10 and 11, more than one magnification display window 67 can be provided, allowing a close-up comparison between images taken at different times, at different angles, or of different medical imaging modalities. Image contrast adjustment may use a breast mask as described in the commonly assigned application entitled AUTOMATIC IMAGE CONTRAST IN COMPUTER-AIDED DIAGNOSTICS by Zhang et al. Ser. No. 11/285,231, noted above Contrast adjustment can be performed using a number of different automated methods for optimizing contrast, well known to those skilled in the imaging arts.

As was discussed with reference to step F2, the viewing radiologist can tag ROI areas during detailed review step F3. Tagging can be performed, for example, using magnification display window 67. Typically, the radiologist pauses scanning so that an ROI can be more accurately located. Alternately, tagging can be performed using the high-resolution display itself, without using the electronic magnifying glass capability. Commands for tagging ROIs can be entered using any of a number of operator entry mechanisms, as described earlier.

Figure 12:
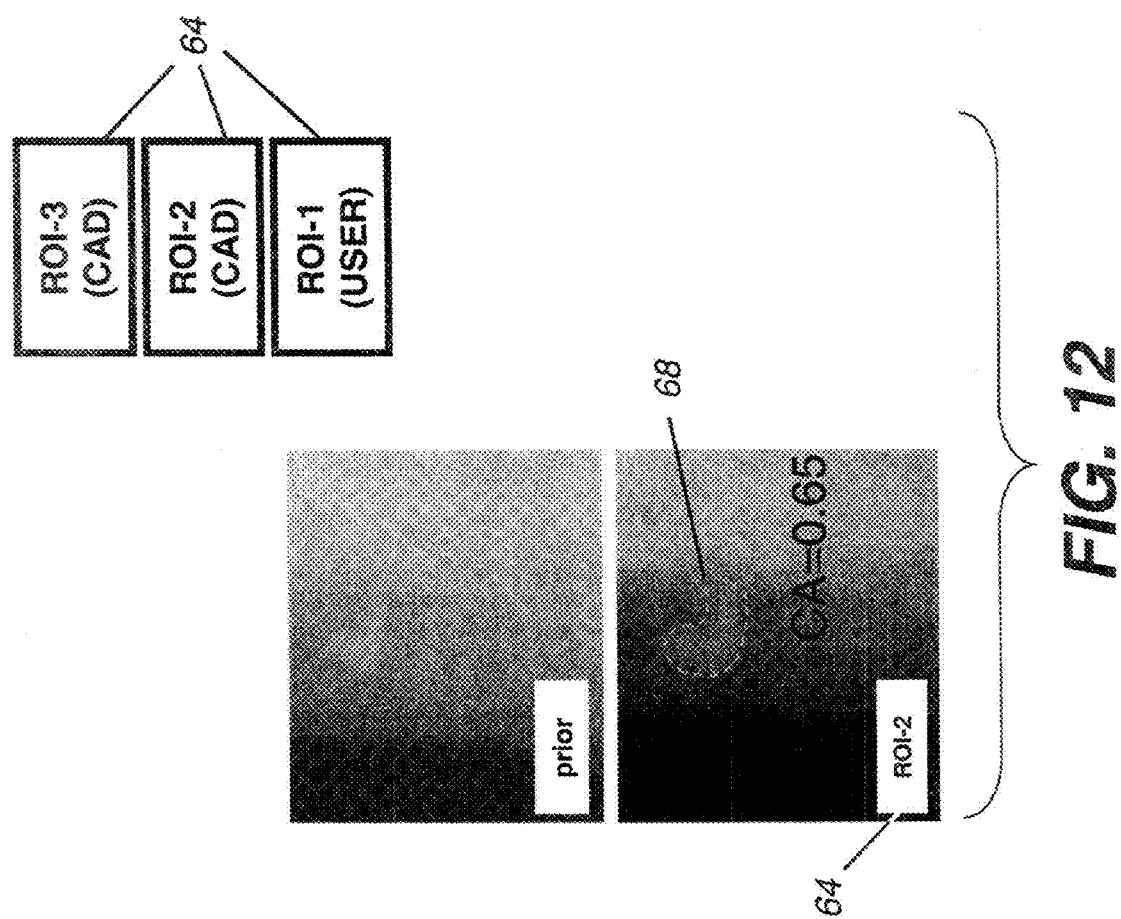
FIG. 12 is a plan view showing formation of an ROI list according to one embodiment.

ROI List Review As one result of initial and detailed review steps F2 and F3, an ROI list is formed, based both on ROIs identified by the diagnostician and any ROIs reported by the CAD system. Referring back to FIG. 5, an ROI list review step F5 follows, in which the combined results of preceding steps and processing are available to the radiologist for assessment and diagnosis. The ROI list, available from navigation monitor 52, identifies the suspect areas for the radiologist. FIG. 12 shows an example of a small ROI list having three entries. Here, ROI-1 is an area detected by the diagnostician, during one of initial and detailed review steps F2 and F3. ROI-2 and ROI-3 are detected from CAD system processing at algorithm server 20 in this example. ROI list review step F4 is used to sort through each item in the ROI list that has been generated and to eliminate ROIs that are not likely candidates from screening.

In one embodiment, as shown in FIG. 12, the ROI list for a patient displays on navigation monitor 52. To work through the list, the viewing physician instructs the system to display a selected ROI entry, then uses the viewing, zooming, and other image manipulation capabilities of the system to display the ROI at a suitable magnification and with suitable image contrast for classifying each ROI, making a determination as to the degree of concern as a possible health risk. The diagnostician may, for example, classify each ROI with a rating (high risk, suspicious, benign, likely benign, etc.) or may eliminate a particular ROI entry from the ROI list. In one embodiment, ROI ratings for each entry in the ROI list are automatically assigned by the CAD system, so that they can be reviewed and edited as necessary by the viewing diagnostician.

The system provides a number of utilities that assist in ROI list review step F4. These include temporal comparison that correlates each ROI from the ROI list with a corresponding region from prior exam results, where available. This can be used, for example, to help the radiologist to assess lesion growth rate within a given region.

Another useful utility for ROI list processing in ROI list review step F4 relates to segmentation. For this function, CAD processing is used to highlight or otherwise identify a detected lesion, mass, or microcalcification. The plan view of FIG. 12 shows tags 64 and an optional outlining 68 that can serve as a type of highlight for the ROI in a segmented view. Tag 64 shown along with the image may identify the source of ROI detection, whether by the CAD system itself or by the radiologist during the review procedures described earlier. Where additional operator input is requested for a tagged area (such as a brief description), a blinking cursor could be provided to indicate incomplete information for a particular ROI.

There may be additional information associated with a particular ROI, such as results reported from image assessment algorithms executed on algorithm server 20. Where additional information is available, an operator instruction, such as an appropriate touchscreen contact, can be used to obtain this information. For example, the image processing algorithms may indicate why an area was tagged as an ROI, such as where there is significant asymmetry, suspicious structure shape or position, density anomaly, and so on.

An automated description of each ROI can also be generated, such as in response to a radiologist request. For calcifications, data reported from algorithm server 20 may indicate morphological characteristics of interest. A calcification may be classified in a number of ways, such as amorphous, coarse heterogeneous, fine pleomorphic, fine linear, skin, vascular, popcorn-like, large rod-like, round, lucent-centered, eggshell, milk, suture, dystrophic. An area may be tagged where there is growth of a structure between earlier and later exams, calling attention to a particular ROI. A tagged location can alternately also be reported back to algorithm server 20 (FIG. 4) to invoke additional localized processing, for example. With a touchscreen embodiment, touching the displayed tag 64 may invoke a separate information window on navigation monitor 52 or on either display monitor 54a, 54b.

One type of localized processing that can be performed for a tagged ROI uses combined results from multiple medical imaging modalities. In this way, additional data can be used to help to profile a particular ROI, thus taking advantage of the strengths of two or more imaging methods. This can include data from any number of prior exams for the patient, helping to identify suspect change patterns for particular features.

In this workflow, the object of ROI review step F4 is to classify each of the ROIs in the ROI list that has been generated using steps F2 and F3. The diagnostician can also add or remove ROIs from the ROI list that has been generated in this manner.

Report Generation Referring again to FIG. 5, a report generation step F5 enables information generated by the CAD system, in cooperation with information contributed by the diagnostician, to be provided in a detailed assessment for the patient. This helps to summarize results and to provide data that assists in making a more accurate diagnosis.

Figure 13:
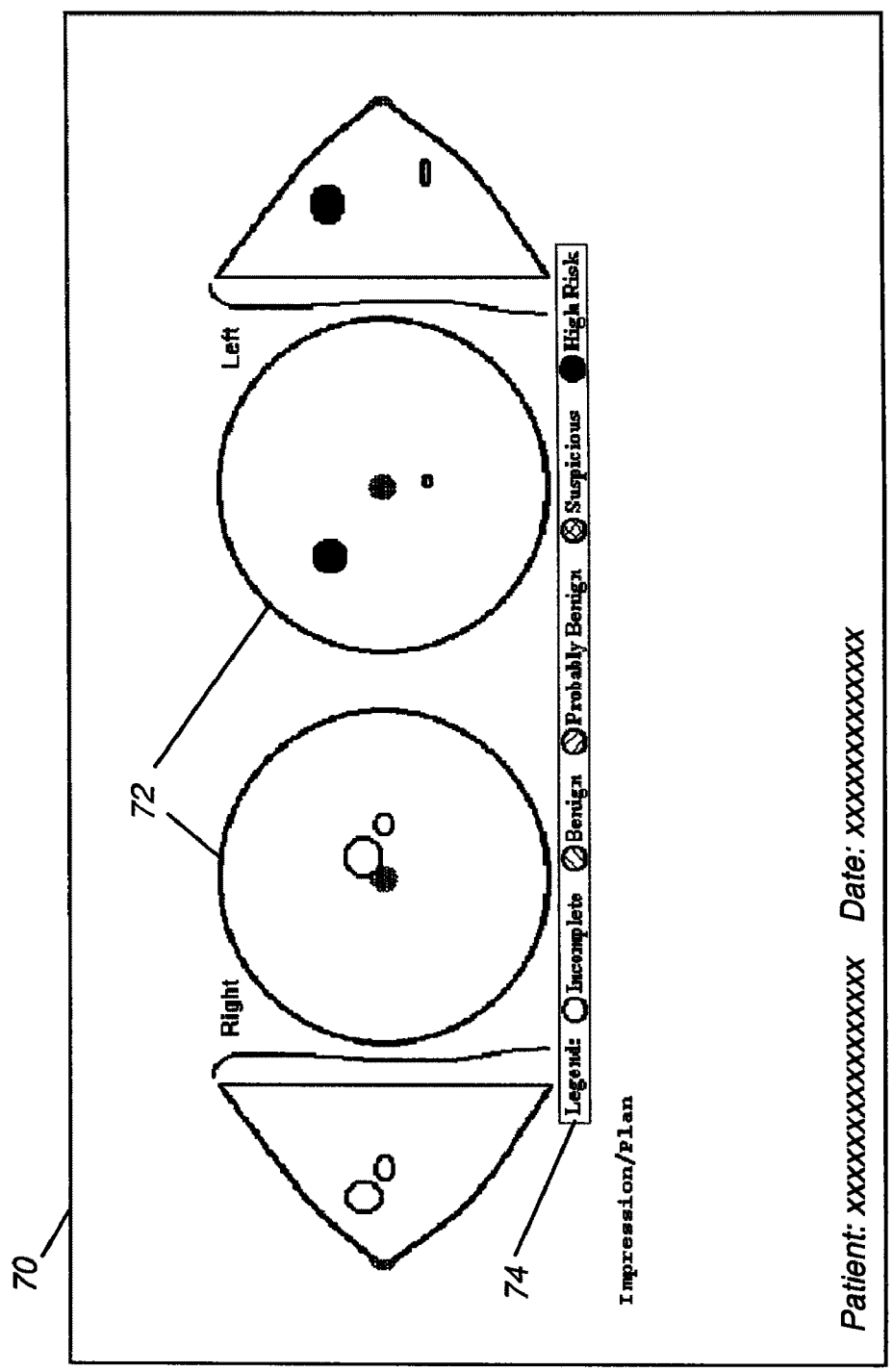
FIG. 13 is a portion of a report generated based on displayed results from a CAD system in one embodiment.

Upon operator command indicating that diagnosis is completed, the system of the present invention automatically generates a report for a patient, summarizing information detected by the CAD system and ROI tag information added by the diagnostician and including any additional comments or confirmation from diagnostic personnel. FIG. 13 shows a portion of a generated report 70, showing areas of concern identified against an outline of breast structures 72 for the patient. A legend 74 is also provided for the symbols used. As is shown in this example, each ROI can be classified according to its likelihood as a cancer site. This profile information could be generated as a file, to be available in printed form as well as maintained for the patient, archived at storage device 22 (FIG. 4), for example. The radiologist can electronically sign the report.

Using the system of the present invention, data on a patient can be stored at storage device 22 and made available for use at a later date, such as for a future exam. This helps to provide continuity, so that a diagnostician can track the progress of an abnormal condition for a particular patient, with prior results readily at hand. ROIs from present exams as well as from past exams could be presented for further processing to algorithm server 20, taking advantage of data obtained over an interval of time in order to track tissue changes for a patient. The present invention takes advantage of what algorithm server 20 of CAD apparatus 40 provides for initial diagnostic assessment of image data, where the system itself identifies and tags ROIs. The system allows a diagnostician to identify one or more ROIs for assessment by the system.

The present invention is adaptable for a multi-modality workflow, providing a method and structures for display of combined results obtained using images from different medical imaging modalities. That is, using techniques of the present invention, imaging data from diverse equipment including X-ray systems, mammography systems, ultrasound (US) apparatus, Magnetic Resonance Imaging (MRI) equipment, and other sources could be combined and used in image processing algorithms as well as displayed in compatible formats for assisting the diagnostician.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, one, two, three or more display monitors could be used, depending on the type and complexity of the images obtained. Navigation of images could be performed without a separate navigation monitor, using commands entered at a keyboard, for example. Hanging protocols could be incorporated into other standard presentation schemes. CAD markings or highlighting of different types could be used to assist in identifying areas of interest. Operator instructions or annotations can be obtained from touchscreen or keyboard entry, as well as from stylus, mouse, or other cursor movement mechanisms or from voice recognition apparatus, for example. While the method of the present invention is particularly suited for use with a digital mammography system, the invention could also be used with other types of medical imaging apparatus.

Thus, what is provided is a system and methods for an improved workflow for display and use of diagnostic images, particularly for mammography.

PARTS LIST

10. CAD system
12. Image capture device
14a, 14b. Storage device
16. Display
18. Printer
20. Algorithm server
22. Storage device
24. Message queue
28. Command entry apparatus
30. Adapter service
40. CAD apparatus
50. Display system
52. Navigation monitor
54a, 54b. Display monitor
56. Thumbnail image
58a, 58b. Border
60. Workstation
62. View
64, 64'. Tag
66. Magnification outline window
67. Magnification display window
68. Outlining
70. Report
72. Structure
74. Legend
80. Scan pattern
82. Current exam image
84. Prior exam image
F1. Hanging protocol selection step
F2. Initial overview step
F3. Detailed review step
F4. ROI list review step
F5. Report generation step
W0. Patient registration step
W2. Image acquisition step
W4. Image quality control and postprocessing step
W6. Reading and reporting step

The invention claimed is:

1. A method for supporting diagnostic workflow from a medical imaging apparatus, the method comprising the steps of:
    a) obtaining a set of at least two images of a patient, wherein each of the at least two images is of the same anatomical feature of the patient but taken at different time periods;
    b) displaying, on a display, the set of images according to a user-specified image display layout selected from a plurality of image display layouts, and displaying each of the images of said set of images by electronically scanning the displayed images with a magnified view to provide a scanned view by the method comprising the steps of:
        (i) defining a magnification outline window that is smaller than the diagnostic image;
        (ii) positioning the magnification outline window over a portion of the diagnostic image to define a magnified image portion therein;

(iii) displaying, on the display, the magnified image portion in a magnification display window; and (iv) changing the magnified image portion within the magnification display window with a repeated process of: changing the relative position of the magnification outline window according to a scan pattern, thereby redefining the magnified image portion and forming a redefined magnified image portion therein; and displaying the redefined magnified image portion in the magnification display window;

c) associating one or more markers with each of the at least two images, each marker identifying a region of interest in the displayed image of each of the at least two images;

d) generating a list of regions of interest having an entry for each marker associated in step c); and e) assigning a classification to each entry in the list according to possible health risk.

2. The method of claim 1 wherein the step of associating one or more markers includes automatically detecting the region of interest identified by each marker according to tissue characteristics.

3. The method of claim 1 wherein a marker operation is available to a user and wherein the step of associating one or more markers comprises the marker operation of responding to a user instruction for marker assignment.

4. The method of claim 1 wherein a number of utilities including an image processing algorithm are provided that assist in region of interest list review and wherein the step of assigning a classification includes the step of applying an image processing algorithm to detect tissue characteristics.

5. The method of claim 1 wherein the regions of interest identified by the markers in the associating step are presented as a list of regions of interest for review by a user.

6. The method of claim 1 wherein the generating step and the assigning a classification step further includes the step of generating a report that lists the list of regions of interest and the assigned classifications.

7. The method of claim 1 wherein the step of obtaining the set of at least two images is accomplished by obtaining mammography images.

8. The method of claim 1 wherein the step of obtaining the set of at least two images comprises obtaining images either taken at different times of one or more days apart, or taken from different medical imaging modalities.

9. The method of claim 8 further comprising outlining an at least one of the images with a color border.

10. The method of claim 1 wherein the set of at least two images is accomplished by obtaining mammography images, and the step of displaying the set of images comprises automatically adjusting image contrast using a breast mask.

11. The method of claim 1 wherein the set of at least two images is mammography images, and the step of displaying the set of images comprises simultaneously displaying one mammography image from a current exam and one mammography image from a prior exam.

12. The method of claim 1 wherein associating the marker comprises responding to an instruction from a user.

13. A method for supporting diagnostic workflow from a medical imaging apparatus, the method comprising the steps of a) obtaining a set of at least two images of a patient, wherein each of the at least two images is of the same anatomical feature of the patient but taken at different time periods;

b) displaying, on a display, the set of images according to a user-specified image display layout selected from a plurality of image display layouts;

c) associating one or more markers with each of the at least two images, each marker identifying a region of interest in the displayed image of each of the at least two images;

d) electronically scanning the displayed images with a magnified view to provide a scanned view by a method comprising the steps of:
  (i) defining a magnification outline window that is smaller than the diagnostic image;
  (ii) positioning the magnification outline window over a portion of the diagnostic image to define a magnified image portion therein;
  (iii) displaying, on the display, the magnified image portion in a magnification display window; and
  (iv) changing the magnified image portion within the magnification display window with a repeated process of changing the relative position of the magnification outline window according to a scan pattern, thereby redefining the magnified image portion and forming a redefined magnified image portion therein; and displaying the redefined magnified image portion in the magnification display window;

e) generating a list of regions of interest having an entry for each marker associated in step c); and f) assigning a classification to each entry in the list according to possible health risk.

* * * * *